(12) United States Patent
Goldmann et al.

(10) Patent No.: US 7,074,784 B2
(45) Date of Patent: Jul. 11, 2006

(54) MEDICAMENTS AGAINST VIRAL DISEASES

(75) Inventors: Siegfried Goldmann, Am Osterholz 91, 42327 Wuppertal (DE); Jurgen Stoltefuss, Hann (DE); Ulrich Niewohner, deceased, late of Wermelskirchen (DE); by Maria Niewohner, legal representative, Wermelskirchen (DE); Karl-Heinz Schlemmer, Wuppertal (DE); Jorg Keldenich, Wuppertal (DE); Arnold Paessens, Stresemannstr. 51, 42781 Haan (DE); Erwin Graef, Wulfrath (DE); Olaf Weber, Woodbridge, CT (US); Karl Deres, Sinzig (DE)

(73) Assignees: Siegfried Goldmann, Wuppertal (DE); Arnold Paessens, Haan (DE)

( * ) Notice: Subject to any disclaimer, the term of this patent is extended or adjusted under 35 U.S.C. 154(b) by 0 days.

(21) Appl. No.: 10/221,919

(22) PCT Filed: Mar. 5, 2001

(86) PCT No.: PCT/EP01/02442

§ 371 (c)(1),
(2), (4) Date: Mar. 10, 2003

(87) PCT Pub. No.: WO01/68640

PCT Pub. Date: Sep. 20, 2001

(65) Prior Publication Data

US 2003/0232842 A1    Dec. 18, 2003

(30) Foreign Application Priority Data

Mar. 16, 2000 (DE) ............................... 100 12 823

(51) Int. Cl.
*C07D 401/04* (2006.01)
*C07D 401/14* (2006.01)
*C07D 403/04* (2006.01)
*A61K 31/506* (2006.01)
*A61P 1/16* (2006.01)

(52) U.S. Cl. ................... 514/227.8; 544/333; 544/122; 544/60; 514/256; 514/231.5

(58) Field of Classification Search ................ 544/333, 544/60, 122, 59; 514/256, 227.8, 231.5
See application file for complete search history.

(56) References Cited

U.S. PATENT DOCUMENTS 4,822,798 A    4/1989  Stoltefuss et al. .......... 514/225
6,436,943 B1   8/2002  Stoltefuss et al. .......... 514/256

FOREIGN PATENT DOCUMENTS

| EP | 0103796 | 3/1984 |
| WO | 9901438 | 1/1999 |
| WO | 9954312 | 10/1999 |
| WO | 9954326 | 10/1999 |
| WO | 9954329 | 10/1999 |

OTHER PUBLICATIONS

Cecil Textbook of Medicine, 20th Edition vol. 2.*

* cited by examiner

*Primary Examiner*—Kahsay Habte

(57) ABSTRACT

Novel dihydropyrimidines and combinations thereof with other antiviral agents, suitable for combating HBV infections.

14 Claims, No Drawings

MEDICAMENTS AGAINST VIRAL DISEASES

The present invention relates to novel 6-aminoalkyldihydropyrimidines, processes for their preparation and their use as medicaments, in particular for the treatment and prophylaxis of hepatitis B virus infections. The invention also relates to combinations of these dihydropyrimidines with other antiviral agents and, where appropriate, immunomodulators, and to medicaments comprising these combinations, in particular for the treatment and prophylaxis of HBV infections such as hepatitis B.

The hepatitis B virus belongs to the family of hepadna viruses. It causes an acute and/or a persistent/progressive chronic disease. Many other clinical manifestations in the pathological state are also caused by the hepatitis B virus—in particular chronic inflammation of the liver, cirrhosis of the liver and hepatocellular carcinoma. In addition, coinfection with the heptatitis delta virus may have adverse effects on the progress of the disease.

The only agents approved for the treatment of chronic hepatitis are interferon and lamivudine. However, interferon has only moderate activity and has unwanted side effects; although lamivudine has good activity, resistance develops rapidly during treatment and a rebound effect occurs in most cases after discontinuation of the therapy.

EP-B 103 796 discloses dihydropyrimidines attributed with an effect influencing the circulation. WO 99/1438 relates to dihydropyrimidines said to be suitable for the treatment of cerebrovascular ischemia and of pain. WO 99/54312, 99/54326 and 99/54329 relate to dihydropyrimidines suitable for the treatment and prophylaxis of hepatitis.

The present invention relates to compounds of the formula

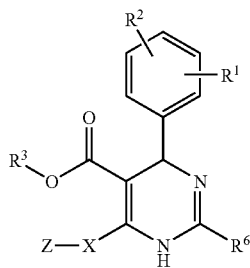

(I)

and the isomeric form thereof

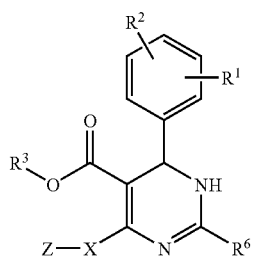

(Ia)

in which
$R^1$, $R^2$ are, independently of one another, hydrogen, fluorine, chlorine or bromine,
$R^3$ is $C_1$–$C_4$-alkyl,
X is a methylene or ethylene group,
Z is $NR^4R^5$ or pyridyl,
$R^4$ is $C_1$–$C_4$-alkyl which may be substituted by hydroxyl or $C_1$–$C_4$-alkoxycarbonyl, or is benzyl,
$R^5$ is $C_1$–$C_4$-alkyl which may be substituted by hydroxyl, or
$R^4$ and $R^4$ together with the nitrogen atom to which they are bonded are an imidazolyl, triazolyl or tetrazolyl ring or a radical of the formula

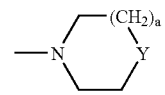

in which
a is zero or 1 and
Y is $CH_2$, $CH_2CH_2$, —O— or —S—,
and
$R^6$ is pyridyl which is substituted once to twice by fluorine, or is thiazolyl,
and the salts thereof.

Preference is given to compounds of the invention of the formulae (I) and (Ia) in which
$R^4$ and $R^5$ together with the nitrogen atom to which they are bonded form a morpholinyl or thiomorpholinyl ring, and the salts thereof.

Particular preference is given to compounds of the invention of the formulae (I) and (Ia) in which
$R^1$, $R^2$ are, independently of one another, fluorine, chlorine or bromine, and the salts thereof.

Very particular preference is given to compounds of the invention of the formulae (I) and (Ia) in which
$R^1$, $R^2$ are, independently of one another, fluorine, chlorine or bromine, and
$R^4$ and $R^5$ together with the nitrogen atom to which they are bonded form a morpholinyl or thiomorpholinyl ring, and the salts thereof.

Alkyl is within the framework of the invention a linear or branched alkyl radical having 1 to 4 carbon atoms, such as, for example, methyl, ethyl, propyl, isopropyl and tert-butyl.

Alkoxycarbonyl is within the framework of the invention a linear or branched alkoxycarbonyl radical having 1 to 4 carbon atoms, such as, for example, methoxycarbonyl, ethoxycarbonyl and propoxycarbonyl.

The compounds of the invention may exist in stereoisomeric forms which either are related as image and mirror image (enantiomers) or are not related as image and mirror image (diastereomers). The invention relates both to the enantiomers or diastereomers and to the respective mixtures thereof. The racemic forms can, just like the diastereomers, be separated in a manner known per se into the stereoisomerically uniform components.

The compounds of the invention include the isomers of the formulae (I) and (Ia) and the mixtures thereof. The compounds of the invention may also be in the form of salts. Physiologically acceptable salts are preferred within the framework of the invention.

Physiologically acceptable salts may be salts of inorganic or organic acids. Preference is given to salts of inorganic acids such as, for example, hydrochloric acid, hydrobromic acid, phosphoric acid or sulfuric acid, or salts of organic carboxylic or sulfonic acids such as, for example, acetic acid, maleic acid, fumaric acid, malic acid, citric acid, tartaric acid, lactic acid, benzoic acid or methanesulfonic acid, ethanesulfonic acid, phenylsulfonic acid, toluene-sulfonic acid or naphthalene-disulfonic acid.

Physiologically acceptable salts may also be metal or ammonium salts of the compounds of the invention. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

The compounds (I) of the invention can be prepared by
[A] firstly converting aldehydes of the formula

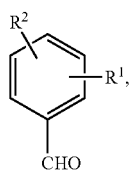
(II)

in which $R^1$ and $R^2$ have the meanings indicated above, with β-ketoesters of the formula

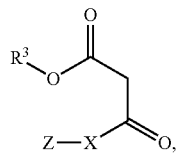
(III)

in which $R^3$, X and Z have the meanings indicated above, with or without addition of base or acid, where appropriate in the presence of inert organic solvents, into benzylidene compounds of the formula

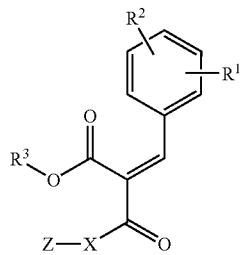
(IV)

and then reacting the latter with amidines of the formula

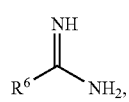
(V)

in which $R^6$ has the meaning indicated above, or the salts thereof (such as, for example, hydrochlorides or acetates) with or without addition of base or acid, where appropriate in the presence of inert organic solvents, or

[B] reacting compounds of the formula (III) in a one-stage process with aldehydes (II) and amidines (V) or salts thereof (such as, for example, hydrochlorides or acetates) with or without addition of base or acid, where appropriate in the presence of inert organic solvents, or else

[C] where X in formula (I) is a methylene group, reacting compounds of the formula

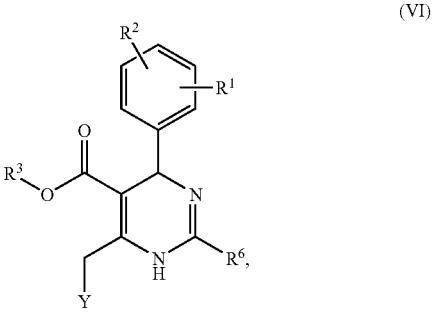
(VI)

in which $R^1$, $R^2$, $R^3$ and $R^6$ have the meanings indicated above, and

Y is a nucleophilically replaceable group such as chloride, bromide, iodide, mesylate or tosylate, with compounds of the formula

(VII)

in which $R^4$ and $R^5$ have the meanings indicated above, with or without addition of a base, where appropriate in inert solvents.

The compounds (VI) can be prepared, for example, by converting compounds of the formula

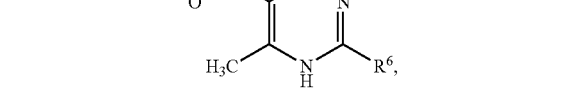
(VIII)

in which $R^1$, $R^2$, $R^3$ and $R^6$ have the meanings indicated above, with a brominating agent such as, for example, N-bromosuccinimide, preferably in the presence of inert solvents, into compounds of the formula (IX)

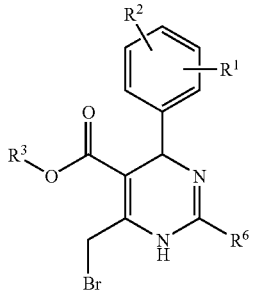

The latter can then be reacted, directly or after further transformation, customary in the literature, of the nucleophilically replaceable group, with compounds (VII).

[D] Where X, in formula (I) is an ethylene group, it is also possible to convert compounds of the formula (X)

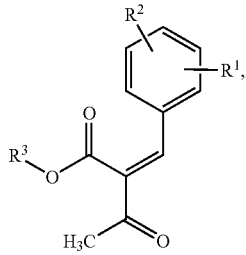

in which $R^1$, $R^2$ and $R^3$ have the meanings indicated above, with immonium salts of the formula (XI)

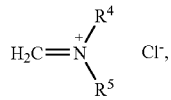

in which $R^4$ and $R^4$ have the meanings indicated above, with or without addition of a base, where appropriate in inert solvents, into compounds of the formula (XII)

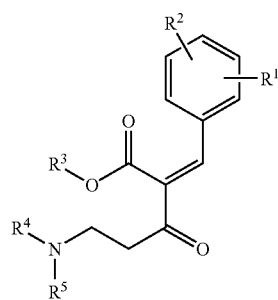

and then to react the latter with amidines (V) or salts thereof (such as, for example, hydrochlorides or acetates) with or without addition of acid or base, where appropriate in the presence of inert organic solvents.

To prepare the compounds of the invention of the formula (I) in which X is a methylene group and Z is the group —NR⁴R⁵, the corresponding β-keto carboxylic esters (III) can also be obtained by reacting chloroacetic esters of the formula (XIII)

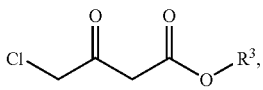

in which $R^3$ has the meaning indicated above, with compounds of the formula (VII).

To prepare the compounds of the invention of the formula (I) in which X is an ethylene group and Z is pyridyl, the corresponding β-keto carboxylic esters (III) can also be obtained by reacting the dianions of acetoacetic esters of the formula (XIV)

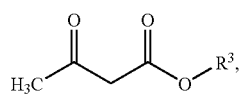

in which $R^3$ has the meaning indicated above, with picolyl derivatives of the formula (XV)

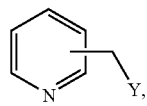

in which

Y has the meaning indicated above.

The aldehydes (II) used as starting materials are known or can be prepared by methods known from the literature [cf. T. D. Harris and G. P. Roth, J. Org. Chem. 44, 146 (1979); DE-A 2 165 260 and 2 401 665; Mijano et al., Chem. Abstr. 59, 13 929 c (1963); E. Adler and H.-D. Becker, Chem. Scand. 15, 849 (1961); E. P. Papadopoulos, M. Mardin and Ch. Issidoridis, J. Org. Chem. Soc. 78, 2543, (1956)].

The β-keto carboxylic esters (III) used as starting materials are known in some cases or can be prepared in analogy to methods known from the literature [e.g. D. Borrmann, "Umsetzung von Diketen mit Alkoholen, Phenolen und Mercaptanen", in "Methoden der Organischen Chemie" (Houben-Weyl), vol. VII/4, 230 ff (1968); Y. Oikawa, K. Sugano und O. Yonemitsu, J. Org. Chem. 43, 2087 (1978)].

The compounds (V) are known in some cases or can be prepared as described in WO-A-99/54326 and WO-A-99/54329.

The compounds (VIII) and (X) can be prepared in accordance with process variants [A] or [B] as described in WO-A-99/54326.

The compounds (VII) and (XI) are known or can be prepared by customary methods.

Solvents suitable for all the process variants A, B, C, D and E are all inert organic solvents. These preferably include alcohols such as methanol, ethanol, isopropanol, ethers such as dioxane, diethyl ether, tetrahydrofuran, glycol monomethyl ether, glycol dimethyl ether, carboxylic acids such as glacial acetic acid, or dimethylformamide, dimethyl sulfoxide, acetonitrile, pyridine and hexamethylphosphoric triamine.

The reaction temperatures may be varied within a relatively wide range. Those used are generally between 20 and 150° C., but preferably at the boiling point of the particular solvent.

The reaction can be carried out under atmospheric pressure but also under elevated pressure. It is generally carried out under atmospheric pressure.

The reaction can be carried out with or without addition of base or acid; however, it is advisable to carry out the reaction in the presence of relatively weak acids such as, for example, acetic acid or formic acid.

Compounds of the formula (IX) are novel; the invention therefore also relates to compounds of the formula (IX).

One embodiment of the invention relates to combinations of A) at least one of the dihydropyrimidines defined above, B) at least one other antiviral agent different from A.

A particular embodiment of the invention relates to combinations of A) above dihydropyrimidines, B) HBV polymerase inhibitors and, where appropriate, C) immunomodulators.

Preferred immunomodulators C) comprise, for example, all interferons such as α-, β- and γ-interferons, in particular also α-2a- and α-2b-interferons, interleukins such as interleukin-2, polypeptides such as thymosin-α-1 and thymoctonan, imidazoquinoline derivatives such as ®Levamisole, immunoglobulins and therapeutic vaccines.

The invention thus also relates to these combinations for the treatment and prophylaxis of HBV infections and to the use thereof for the treatment of HBV-induced diseases.

The use of the combinations of the invention provides valuable advantages for the treatment of HBV-induced diseases compared with monotherapy with the individual compounds, namely principally a synergistic antiviral activity, but also good tolerability of the combinations of the invention in the range of toxicity at which 50% of the cells survive ("Tox-50")—compared with the Tox-50 of the individual components.

The substances referred to as HBV polymerase inhibitors B for the purposes of the invention are those which, in the endogenous polymerase assay which was published by Ph. A. Furman et al. in Antimicrobial Agents and Chemotherapy, Vol. 36 (No. 12), 2688 (1992) and which is described hereinafter, lead to an inhibition of the formation of an HBV DNA double strand, so as to result in a maximum of 50% of the activity of the zero value:

HBV virions from culture supernatants incorporate nucleoside 5'-triphosphates into the plus strand of the HBV DNA in vitro. By using agarose gel electrophoresis, the incorporation of [α-$^{32}$P]-deoxynucleoside 5'-triphosphate into the viral 3.2 kb DNA product is observed in the presence and absence of a substance potentially having HBV polymerase-inhibiting properties. HBV virions are obtained from the cell culture supernatant of HepG2.2.15 cells by precipitation with polyethylene glycol and are concentrated. 1 part by volume of clarified cell culture supernatant is mixed with ¼ by volume of an aqueous solution containing 50% by weight polyethylene glycol 8000 and 0.6 M sodium chloride. The virions are sedimented by centrifugation at 2500× g/15 minutes. The sediments are resuspended in 2 ml of buffer containing 0.05 M tris-HCl (pH 7.5) and dialyzed against the same buffer containing 100 mM potassium chloride. The samples can be frozen at −80° C. Each reaction mixture (100 µl) contains at least $10^5$ HBV virions; 50 mM tris-HCl ($p_H$ 7.5); 300 mM potassium chloride; 50 mM magnesium chloride; 0.1% ®Nonident P-40 (nonionic detergent from Boehringer Mannheim); 10 µM each dATP, dGTP and dTTP; 10 µCi of [$^{32}$P]dCTP (3000 Ci/mmol; final concentration 33 nM) and 1 µM of the potential polymerase inhibitor in its triphosphorylated form. The samples are incubated at 37° C. for one hour and then the reaction is stopped by adding 50 mM EDTA. A 10% weight/volume SDS solution (containing 10 g of SDS per 90 ml of water) is added to a final concentration of 1% by volume (based on the total volume), and proteinase K is added to a final concentration of 1 mg/ml. After incubation at 37° C. for one hour, samples are extracted with the same volume of phenol/chloroform/isoamyl alcohol (ratio 25:24:1 by volume), and the DNA is precipitated from the aqueous phase with ethanol. The DNA pellet is resuspended in 10 µl of gel buffer (solution of 10.8 g of tris, 5.5 g of boric acid and 0.75 g of EDTA in 1 liter of water (=TBE buffer)) and separated by electrophoresis in an agarose gel. Either the gel is dried or the nucleic acids present therein transferred by the Southern transfer technique to a membrane. The amount of labeled DNA double strand formed is then determined in relation to the negative control (=endo-pol reaction without substance or with inactive control substance). An HBV polymerase inhibitor is present if a maximum of 50% of the activity of the negative control is present.

Preferred HBV polymerase inhibitors B) comprise, for example,

3TC=lamivudine==4-amino-1-[(2R-cis)-2-(hydroxymethyl)-1.3-oxathiolan-5-yl]-pyrimidin-2(1H)-one, cf. EP-B 382 526 (=U.S. Pat. No. 5,047,407) and WO 91/11186 (=U.S. Pat. No. 5,204,466);

Adefovir dipivoxil=9-{2-[[bis[(pivaloyloxy)-methoxy]-phosphinyl]-methoxy]-ethyl}-adenine, cf. EP-B 481 214 (=U.S. Pat. Nos. 5,663,159 and 5,792,756), U.S. Pat. Nos. 4,724,233 and 4,808,716;

BMS 200 475=[1S-(1.α,3.α,4.β)]-2-amino-1.9-dihydro-9-[4-hydroxy-3-(hydroxymethyl)-2-methylene-cyclopentyl]-6H-purin-6-one, cf. EP-B 481 754 (=U.S. Pat. Nos. 5,206,244 and 5,340,816), WO 98/09964 and 99/41275;

Abacavir=(−)-(1S-cis)-4-[2-amino-6-(cyclopropylamino)-9H-purin-9-yl]-2-cyclopentene-1-methanol, cf. EP-B 349 242 (=U.S. Pat. No. 5,049,671) and EP-B 434 450 (=U.S. Pat. No. 5,034,394);

FTC=(2R-cis)-4-amino-5-fluoro-1-[2-(hydroxymethyl)-1.3-oxathiolan-5-yl]-pyrimidin-2(1H)-one, cf. WO 92/14743 (=U.S. Pat. Nos. 5,204,466, 5,210,085, 5,539,116, 5,700, 937, 5,728,575, 5,814,639, 5,827,727, 5,852,027, 5,892, 025, 5,914,331, 5,914,400) and WO 92/18517;

β-L-FDDC=5-(6-amino-2-fluoro-9H-purin-9-yl)-tetrahydro-2-furanmethanol, cf. WO 94/27616 (=U.S. Pat. Nos. 5,627,160, 5,561,120, 5,631,239 and 5,830,881);

L-FMAU=1-(2-deoxy-2-fluoro-β-L-arabinofuranosyl)-5-methyl-pyrimidine-2.4(1H,3H)-dione, cf. WO 99/05157, WO 99/05158 and U.S. Pat. No. 5,753,789.

A further preferred embodiment of the invention relates to combinations of A) above dihydropyrimidines (I) and (Ia) and B) lamivudine.

Other preferred HBV antiviral agents B comprise, for example, phenylpropenamides of the formula

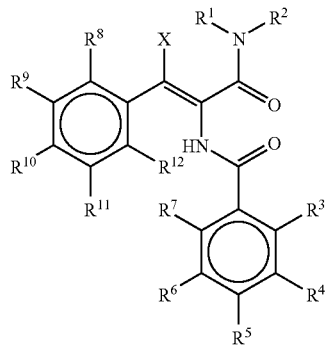

in which

R[1] and R[2] are, independently of one another, $C_{1-4}$-alkyl or, together with the nitrogen atom on which they are located, form a ring having 5 to 6 ring atoms which comprise carbon and/or oxygen, R[3] to R[12] are, independently of one another, hydrogen, halogen, $C_{1-4}$-alkyl, optionally substituted $C_{1-4}$-alkoxy, nitro, cyano or trifluoromethyl, R[13] is hydrogen, $C_{1-4}$-alkyl, $C_{1-7}$-acyl or aralkyl and X is halogen or optionally substituted $C_{1-4}$-alkyl, and the salts thereof.

These phenylpropenamides and processes for preparing them are disclosed in WO 98/33501, to which reference is hereby made for the purpose of the disclosure. AT-61 is the compound of the above formula in which X is chlorine, A is 1-piperidinyl and Y and Z are each phenyl.

Preferred immunomodulators C) comprise, for example, all interferons such as α-, β- and γ-interferons, in particular also α-2a- and α-2b-interferons, interleukins such as interleukin-2, polypeptides such as thymosin-α-1 and thymoctonan, imidazoquinoline derivatives such as ®Levamisole, immunoglobulins and therapeutic vaccines.

A further preferred embodiment of the invention relates to combinations of A) above dihydropyrimidines (I) and (Ia), B) lamivudine and, where appropriate, C) interferon.

Description of Tests

The antiviral action of the compounds of the invention on hepatitis B virus was investigated by methods based on those described by M. A. Sells et al., Proc. Natl. Acad. Sci. 84, 1005–1009 (1987) and B. E. Korba et al., Antiviral Research 19, 55–70 (1992).

The antiviral tests were carried out in 96-well microtiter plates. The first vertical row of the plate received only growth medium and HepG2.2.15 cells. It served as virus control.

Stock solutions of the test compounds (50 mM) were initially dissolved in DMSO, and further dilutions were prepared in the HepG2.2.15 growth medium. The compounds according to the invention were usually pipetted in a test concentration of 100 μM (1st test concentration) in each case into the second vertical test row of the microtiter plate and subsequently diluted in twofold steps $2^{10}$ times in growth medium plus 2% by weight of fetal calf serum (volume 25 μl).

Each well of the microtiter plate then contained 225 μl of HepG2.2.15 cell suspension ($5 \times 10^4$ cells/ml) in growth medium plus 2% by weight of fetal calf serum. The test mixture was incubated at 37° C. and 5% $CO_2$ (v/v) for 4 days.

The supernatant was then aspirated off and discarded, and the wells received 225 μl of freshly prepared growth medium. The compounds according to the invention were each added anew as 10-fold concentrated solution in a volume of 25 μl. The mixtures were incubated for a further 4 days.

Before harvesting the supernatants to determine the antiviral effect, the HepG2.2.15 cells were examined under the light microscope or by means of biochemical detection methods (for example Alamar Blue stain or Trypan Blue stain) for cytotoxic changes.

The supernatant and/or cells were then harvested and sucked by means of a vacuum onto 96-well dot-blot chambers covered with a nylon membrane (in accordance with the manufacturer's information).

Cytotoxicity Determination

Substance-induced cytotoxic or cytostatic changes in the HepG2.2.15 cells were detected, for example, under the light microscope as changes in cell morphology. Such substance-induced changes in the HepG2.2.15 cells compared with untreated cells were visible, for example, as cytolysis, vacuolation or altered cell morphology. 50% cytotoxicity (Tox.-50) means that 50% of the cells show a morphology comparable to the corresponding cell control.

The tolerability of some of the compounds according to the invention was additionally tested on other host cells such as, for example, HeLa cells, primary human peripheral blood cells or transformed cell lines such as H-9 cells.

No cytotoxic changes were detectable at concentrations >10 μM of the compounds of the invention.

Determination of the Antiviral Action

After the supernatants or lysed cells had been transferred to the nylon membrane of the blot apparatus (see above), the intra- or extracellular supernatants of the HepG2.2.15 cells were denatured (1.5 M NaCl/0.5 N NaOH), neutralized (3 M NaCl/0.5 M Tris HCl, pH 7.5) and washed (2×SSC). The DNA was then baked onto the membrane by incubating the filters at 120° C. for 2–4 hours.

DNA Hybridization

Detection of the viral DNA from the treated HepG2.2.15 cells on the nylon filters was usually carried out with nonradioactive, digoxigenin-labeled hepatitis B-specific DNA probes, each of which was labeled with digoxigenin, purified and employed for the hybridization in accordance with the manufacturer's information.

The prehybridization and hybridization took place in 5×SSC, 1× blocking reagent, 0.1% by weight N-lauroylsarcosine, 0.02% by weight SDS and 100 μg of herring sperm DNA. The prehybridization took place at 60° C. for 30 minutes, and the specific hybridization with 20 to 40 ng/ml of the digoxigenized, denatured HBV-specific DNA (14 hours, 60° C.). The filters were then washed.

Detection of HBV-DNA by Digoxigenin Antibodies

The immunological detection of the digoxigenin-labeled DNA took place in accordance with the manufacturer's information:

The filters were washed and prehybridized in a blocking reagent (in accordance with the manufacturer's information). Hybridization was then carried out with an anti-DIG antibody coupled to alkaline phosphatase for 30 minutes. After a washing step, the substrate of alkaline phosphatase, CSPD, was added, incubated with the filters for 5 minutes, then packed in plastic film and incubated at 37° C. for a further 15 minutes. The chemiluminescence of the hepatitis B-specific DNA signals was visualized by exposing the filters to an X-ray film (incubation depending on signal strength: 10 minutes to 2 hours).

The half-maximum inhibitory concentration ($IC_{50}$, 50% inhibitory concentration) was determined as the concentration at which the intra- or extracellular hepatitis B-specific band was reduced by the compound according to the invention by 50% compared with an untreated sample.

The compounds of the invention show a valuable antiviral action which could not have been predicted. They surprisingly show antiviral activity against hepatitis B viruses (HBV) since they cause an extremely large reduction in intra- and/or extracellular HBV DNA. The compounds of the invention are thus suitable for the treatment of virus-induced diseases, in particular of acutely and chronically persistent viral infections by HBV. A chronic viral disease caused by HBV may lead to pathological states varying in severity, and chronic hepatitis B viral infection is known in many cases to lead to cirrhosis of the liver and/or hepatocellular carcinoma.

Areas of indication which may be mentioned for the compounds of the invention are, for example:
the treatment of acute and chronic viral infections which may lead to infectious hepatitis, for example infections with heptatitis B viruses. The compounds of the invention are particularly suitable for the treatment of chronic hepatitis B infections and the treatment of acute and chronic hepatitis B viral infections.

The present invention includes pharmaceutical preparations which, besides nontoxic, inert pharmaceutically suitable carriers, comprise one or more compounds (I) or (Ia) or a combination of the invention or which consist of one or more active ingredients (I) or (Ia) or of a combination of the invention.

The active ingredients (I) and (Ia) are intended to be present in the pharmaceutical preparations mentioned above in a concentration of about 0.1 to 99.5% by weight, preferably of about 0.5 to 95% by weight, of the complete mixture.

The pharmaceutical preparations mentioned above may also comprise other active pharmaceutical ingredients apart from the compounds (I) and (Ia).

The ratio of the amounts of the components A, B and, where appropriate, C in the combinations of the invention may vary within wide limits; it is preferably 5 to 500 mg of A/10 to 1000 mg of B, in particular 10 to 200 mg of A/20 to 400 mg of B.

Component C, which is also to be used where appropriate, may be used in amounts of, preferably, 1 to 10 million, in particular 2 to 7 million, I.U. (international units), about three times a week over a period of up to one year.

The compounds or combinations of the invention are intended to be present in the pharmaceutical preparations mentioned above in general in a concentration of about 0.1 to 99.5, preferably about 0.5 to 95, % by weight of the complete mixture.

The pharmaceutical preparations mentioned above can be produced in a conventional way by known methods, for example by mixing the active ingredient(s) with the carrier(s).

It has generally proved to be advantageous both in human and in veterinary medicine to administer the active ingredient(s) in total amounts of about 0.5 to about 500, preferably of 1 to 100 mg/kg of body weight every 24 hours, where appropriate in the form of a plurality of single doses, to achieve the desired results. A single dose contains the active ingredient(s) preferably in amounts of about 1 to about 80, in particular 1 to 30, mg/kg of body weight. However, it may be necessary to deviate from the dosages mentioned, in particular depending on the species and body weight of the subject to be treated, the nature and severity of the disorder, the type of preparation and mode of administration of the medicament, and the time or interval within which administration takes place.

The invention therefore relates further to the compounds and combinations defined above for controlling diseases.

The invention further relates to medicaments comprising at least one of the compounds or combinations defined above and, where appropriate, one or more other active pharmaceutical ingredient(s).

The invention further relates to the use of the compounds and combinations defined above for producing a medicament for the treatment and prophylaxis of the diseases described above, preferably of viral diseases, in particular of hepatitis B.

The percentage data in the following examples relate in each case to weight unless indicated otherwise. The ratios of solvents in solvent mixtures are in each case based on volume.

EXAMPLES

A. Starting Compounds

Example I

3-Fluoropyridine N-oxide

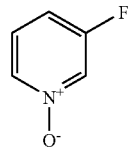

22.20 ml of $H_2O_2$ (30% strength) are added to a solution of 11.10 g (114.324 mmol) of 3-fluoropyridine in 74.00 ml of acetic acid, and the mixture is stirred at a bath temperature of 100° C. for 7 hours. It is then concentrated to 30 ml and, after addition of 30 ml of water, again concentrated to 30 ml. The solution is stirred with dichloromethane, basified by addition of $K_2CO_3$ and separated, and the aqueous phase is extracted twice with dichloromethane, dried and concentrated.

Yield: 11.5 g (88.9%)

Melting point: 66–68° C.

Example II

2-Cyano-3-fluoropyridine

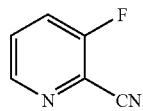

5.20 g (45.980 mmol) of the compound from Example I are dissolved in 50 ml of acetonitrile. Under argon, 13.70 g (138.092 mmol) of trimethylsilylnitrile are added and 12.80 ml of triethylamine are slowly run in. The solution is stirred under reflux for 7 hours and then at room temperature overnight. Concentration using a waterpump is followed by taking up in dichloromethane, shaking twice with 50 ml of 2N aqueous sodium carbonate solution, washing with water, drying and concentrating.

Yield (crude): 5.3 g (oil)

Column chromatography: methylene chloride to methylene chloride/ethyl acetate (10:1)

Example III

2-Amidino-3-fluoropyridine hydrochloride

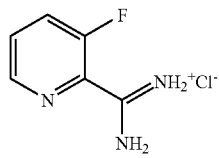

A sodium methoxide solution made from 0.40 g (17.391 mmol) of sodium and 65 ml of methanol is added to a solution of 10.30 g (84.355 mmol) of the compound from Example II in 30 ml of methanol, and the mixture is stirred at 20° C. for 72 hours. 5.44 g (101.682 mmol) of ammonium chloride (powdered) and 17.39 mmol (1.04 ml) of acetic acid are added, and the mixture is stirred at 40° C. for 28 hours and cooled. Insoluble salt is filtered off with suction (1.78 g), and the filtrate is concentrated, concentrated with acetone and then stirred with acetone, filtered off with suction and washed.

Yield: 10.6 g

Melting point: ≈150° C. decomposition

Example IV

2-Cyano-3,5-dichloropyridine

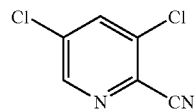

Method 1:

21.8 ml (0.174 mmol) of trimethylsilyl cyanide and 14.6 ml (0.158 mmol) of dimethylcarbamoyl chloride are added successively to a solution of 26 g (0.158 mol) of 3,5-dichloropyridine 1-oxide (Johnson et al., J. Chem. Soc. B, 1967, 1211) in 80 ml of dichloromethane and stirred at room temperature for 48 hours. 100 ml of a 10% strength aqueous $NaHCO_3$ solution are added, and the mixture is vigorously stirred for 10 minutes. Separation of the phases is followed by extraction once with dichloromethane; the combined organic phases are dried and concentrated. The residue is chromatographed on silica gel with dichloromethane and recrystallized from a little methanol.

11 g (40.2%) of 2-cyano-3,5-dichloropyridine (melting point: 102° C.) are obtained.

Method 2:

In analogy to Troschuetz, R. et al., J. Heterocycl. Chem. 33, 1815–1821 (1996), 150 ml of diethylene glycol dimethyl ether, 47.68 g (0.261 mol) of 2,3,5-trichloro-pyridine, 2.0 g (0.005 mol) of tetraphenylphosphonium bromide, 4.0 g (0.024 mol) of finely powdered potassium iodide and 75.0 g (0.838 mol) of copper(I) cyanide are mixed under nitrogen and stirred under reflux for 24 hours. Then a further 100 ml of diethylene glycol dimethyl ether, 2.0 g (0.005 mol) of tetraphenylphosphonium bromide, 4.0 g (0.024 mol) of finely powdered potassium iodide and 75 g (0.838 mol) of copper(I) cyanide are added, and the mixture is stirred at reflux temperature for a further 89 hours. Cooling to room temperature is followed by filtration with suction, and the filtrate is distilled to remove most of the diethylene glycol dimethyl ether. The residue is taken up in toluene and washed with an aqueous solution of Mohr's salt and then with aqueous $NaHCO_3$ solution (peroxide test). It is then washed with water to remove diethylene glycol dimethyl ether. After filtration through cellit, the filtrate is dried over magnesium sulfate, and the solution is concentrated.

18.0 g (40.0%) of 2-cyano-3,5-dichloropyridine are obtained.

Example V

2-Cyano-3,5-difluoropyridine

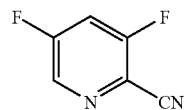

50 g (0.29 mol) of 2-cyano-3,5-dichloropyridine from Example IV, 33.6 g (0.58 mol) of potassium fluoride and 10 g of polyethylene glycol 8000 are mixed with 125 ml of DMSO and heated at 160° C. for 30 minutes. After cooling, the product is distilled out together with the DMSO under high vacuum, the distillate is added to water and, after extraction with toluene, dried over sodium sulfate. The product is reacted further as solution in toluene.

$R_f$: 0.43 (cyclohexane/ethyl acetate=7:3)

Example VI 3,5-Difluoro-2-pyridinecarboximidamide hydrochloride

328 ml of trimethylaluminum (2 M in hexane, 0.624 mol) are added dropwise to a suspension, cooled to 0 to 5° C., of 33.4 g (0.624 mol) of ammonium chloride in 1 l of toluene; the mixture is stirred at room temperature until methane evolution has ceased. The solution of 2-cyano-3,5-dichloropyridine from Example V in toluene is then added dropwise, and the mixture is subsequently stirred at 80° C. overnight. After cooling to 0 to –5° C., methanol is added dropwise until gas evolution ceases, and the salts are filtered off with suction and washed twice with a little methanol. The solvent is stripped off, the residue is dissolved in 500 ml of dichloromethane/methanol (9:1) and again filtered with suction to remove inorganic salts. 23.6 g (39.1%) of 3,5- difluoro-2-pyridinecarboximidamide hydrochloride (melting point: 183° C.) remain after the solvent has been stripped off.

$^1$H-NMR (DMSO-D$_6$): 8.3–8.45 (m, 1H) ppm; 8.8 (d, J=2 Hz, 1H) ppm; 9.7 (s, broad, 4H) ppm.

Example VII

Methyl 2-acetyl-3-(2-chloro-4-fluorophenyl)acrylate

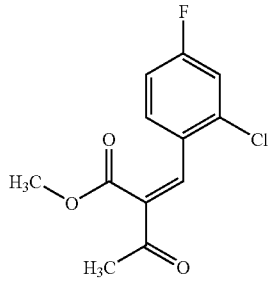

1.7 ml of piperidine acetate are added to a solution of 50 g (315 mmol) of 2-chloro-4-fluorobenzaldehyde and 36.6 g (315 mmol) of methyl acetoacetate in 150 ml of isopropanol. Stirring at room temperature overnight is followed by dilution with dichloromethane and extraction with water, and the organic phase is dried over sodium sulfate and concentrated. The product is reacted further as a crude cis/trans mixture.

Example VIII

Methyl 4-(4-morpholinyl)-3-oxobutanoate

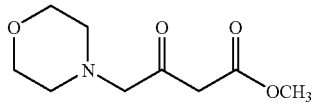

1.27 g (14.6 mmol) of morpholine are added to a solution of 1.0 g (6.64 mmol) of methyl 4-chloroacetoacetate in 10 ml of dichloromethane, and the mixture is stirred at room temperature for 4 hours. Water is then added and the mixture is neutralized with 2N hydrochloric acid. The organic phase is dried over sodium sulfate and concentrated, and the residue is chromatographed on silica gel with cyclohexane/ethyl acetate (10:1→4:1→1:1) as mobile phase.

Yield: 0.475 g (35.5)

Example IX

Methyl 3-(2-chloro-4-fluorophenyl)-2-[3-(1,3-thiazolidin-3-yl)-propanoyl]-acrylate

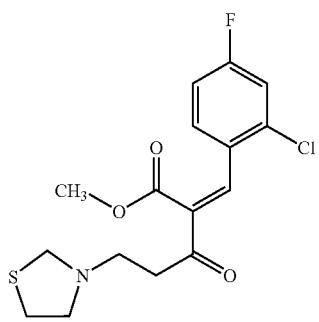

3.24 g (12.6 mmol) of methyl 2-acetyl-3-(2-chloro-4-fluorophenyl)acrylate from Example VII are stirred with 1.74 g (12.6 mmol) of 3-methylene-1,3-thiazolidin-3-ium chloride [prepared in analogy to H. Mohrle et al., Z. Naturforsch. 42, 1035–1046 (1987)] in 50 ml of acetonitrile at 40° C. for 48 hours. After concentration, the residue is taken up in ethyl acetate and washed with water. The organic phase is dried over sodium sulfate and concentrated, and the residue is chromatographed on silica gel with cyclohexane/ethyl acetate (5:1→2:1) as mobile phase.

Yield: 0.67 g (14.8%)

Example X

Methyl 3-oxo-5-(4-pyridinyl)-pentanoate

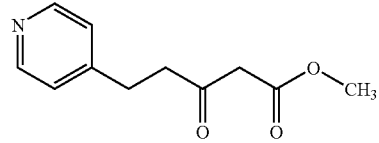

10.0 g (86.1 mmol) of methyl acetoacetate are added dropwise to 3.62 g (90.5 mmol) of sodium hydride (as 60% suspension in mineral oil) in 150 ml of THF at 0° C. After stirring at 0° C. for a further 20 minutes, 53 ml of a 1.6 molar solution of n-butyl-lithium in hexane are added dropwise and then, after stirring for 10 minutes, a solution of 14.1 g (86.1 mmol) of 4-picolyl chloride in 65 ml of THF is added. Stirring at room temperature overnight is followed by neutralization with 2N hydrochloric acid and separation of the phases, and the organic phase is dried over sodium sulfate and concentrated, and the crude product is purified by column chromatography on silica gel firstly with petroleum ether/ethyl acetate (4:1) and then with dichloromethane/methanol (9:1) as mobile phase.

Yield: 3.2 g (17.9% of theory)

R$_f$=0.62 (dichloromethane/methanol 10:1)

Example XI

Methyl 3-(2-chloro-4-fluorophenyl)-2-[3-(4-pyridinyl)-propanoyl]-2-propenoate

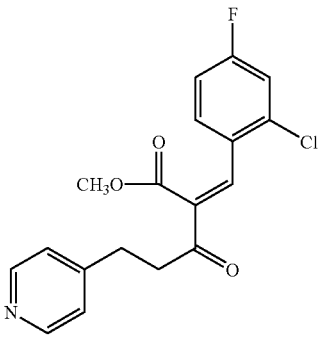

A solution of 2.44 g (15.4 mmol) of 2-chloro-4-fluorobenzaldehyde and 3.19 g (15.4 mmol) of the compound from Example X in 20 ml of isopropanol are mixed with 0.1 ml of piperidine and 0.13 ml of glacial acetic acid. Stirring at room temperature overnight is followed by concentration, and the residue is chromatographed on silica gel with dichloromethane->dichloromethane/methanol (50:1) as mobile phase. The product is employed further as cis/trans mixture.

Yield: 4.5 g (84.0% of theory)

Example XII

Methyl 4-(2-chloro-4-fluorophenyl)-2-(3,5-difluoro-2-pyridinyl)-6-methyl-1,4-dihydropyrimidine-5-carboxylate

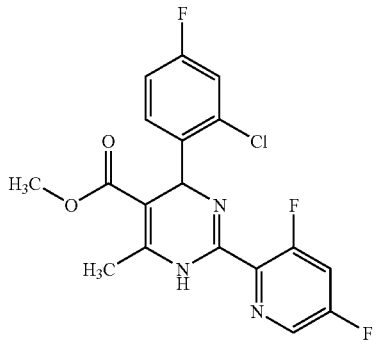

4.5 g (23.2 mmol) of 3,5-difluoro-2-pyridinecarboximidamide hydrochloride from Example VI and 7.7 g (30 mmol) of methyl 2-acetyl-3-(2-chloro-4-fluorophenyl)-2-propenoate from Example VII and 2.3 g (27.9 mmol) of sodium acetate are dissolved or suspended in 120 ml of isopropanol and boiled under reflux for 4 hours. Cooling to room temperature is followed by filtration with suction to remove inorganic salts, and concentration. The residue is taken up in a mixture of 30 ml of 1N hydrochloric acid and 35 ml of ethyl acetate, and the phases are separated. The ethyl acetate phase is back-extracted once with 30 ml of 1N hydrochloric acid. The combined aqueous phases are extracted three times with 10 ml of diethyl ether each time. The aqueous phase is made alkaline with NaOH and extracted with ethyl acetate. The organic phases are dried over sodium sulfate and concentrated.

7.4 g (80%) of product are obtained
Melting point: 126° C.
$^1$H-NMR (DMSO-$D_6$): 2.4 (s, 3H) ppm, 3.5 (s, 3H) ppm, 6.0 (s, 1H) ppm, 7.2 (m, 1H) ppm, 7.4 (m, 2H) ppm, 8.0 (m, 1H) ppm, 8.55 (d, J=2 Hz, 1H) ppm, 9.75 (s, NH) ppm.

The (−)-enantiomer is obtained after separation of the enantiomers on chiral columns (Chiralpak AS from Baker, mobile phase n-heptane/ethanol=8:2).
Melting pont: 117° C. (from ethanol)
$[\alpha]_D^{20}$: −62.8° (methanol)

Example XIII

Methyl (R)-6-bromomethyl-4-(2-chloro-4-fluorophenyl)-2-(3,5-difluoro-2-pyridyl)-1,4-dihydropyrimidine-5-carboxylate

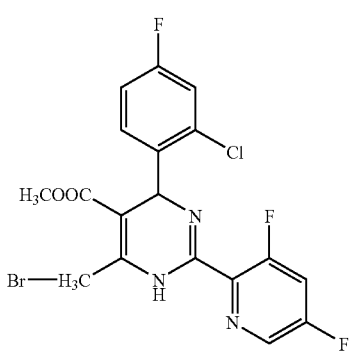

A solution of 2 g (5.05 mmol) of methyl 4-(2-chloro-4-fluorophenyl)-2-(3,5-difluoropyridin-2-yl)-6-methyl-1,4-dihydropyrimidine-5-carboxylate from Example XII in 30 ml of tetrachloromethane is heated to 50° C. under argon, resulting in a clear solution. At this temperature, 0.99 g (5.56 mmol) of N-bromosuccinimide is added, and the mixture is kept at this temperature for 10 minutes. It is immediately cooled, filtered with suction and concentrated under reduced pressure at room temperature. The product is more than 90% pure according to HPLC and is employed further as crude material.

$R_f$=0.33 (cyclohexane/ethyl acetate=7:3)

The following were prepared analogously:

| Example | |
|---|---|
| Example XIV: | Methyl 6-bromomethyl-4-(2,4-dichlorophenyl)-2-(3,5-difluoro-2-pyridyl)-1,4-dihydropyrimidine-5-carboxylate |
| Example XV: | Methyl 6-bromomethyl-4-(2-chlorophenyl)-2-(3,5-difluoro-2-pyridyl)-1,4-dihydropyrimidine-5-carboxylate |
| Example XVI: | Methyl 6-bromomethyl-4-(2,4-difluorophenyl)-2-(3,5-difluoro-2-pyridyl)-1,4-dihydropyrimidine-5-carboxylate |
| Example XVII: | Methyl 6-bromomethyl-4-(2-chloro-4-fluorophenyl)-2-(2-thiazolyl)-1,4-dihydropyrimidine-5-carboxylate |
| Example XVIII: | Methyl 6-bromomethyl-4-(2-bromo-4-fluorophenyl)-2-(2 thiazolyl)-1,4-dihydropyrimidine-5-carboxylate |

B. Preparation Examples

Example 1

Methyl 4-(2-chloro-4-fluorophenyl)-2-(3,5-difluoro-2-pyridyl)-6-(4-morpholinylmethyl)-1,4-dihydropyrimidine-5-carboxylate

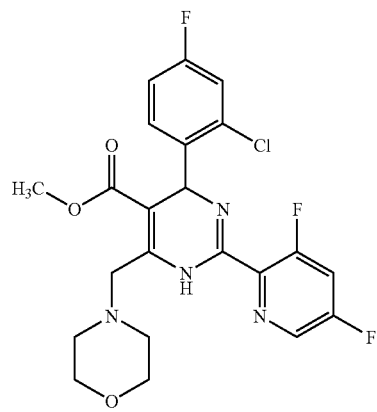

A solution of 0.38 g (2.4 mmol) of 2-chloro-4-fluorobenzaldehyde in 10 ml of isopropanol is heated together with 0.46 g (2.4 mmol) of the compound from Example VI, 0.48 g (2.4 mmol) of the compound from Example VIII and 0.24 g (2.88 mmol) of sodium acetate under reflux for 2 hours. The reaction mixture is concentrated, and the residue is taken up in dichloromethane and extracted with 2N hydrochloric acid. The aqueous phase is made alkaline with dilute ammonia solution and extracted with dichloromethane. The organic phase is washed with aqueous sodium chloride solution, dried over sodium sulfate and concentrated. The residue is chromatographed on silica gel with cyclohexane/ethyl acetate (20:1→10:1) as mobile phase, and the product is crystallized from diethyl ether.

Yield: 0.03 g (2.6%)
Melting point: 190° C.

Example 2

Methyl 4-(2-chloro-4-fluorophenyl)-2-(3,5-difluoro-2-pyridyl)-6-[2-(1,3-thiazolidin-3-yl)-ethyl]-1,4-dihydropyrimidine-5-carboxylate

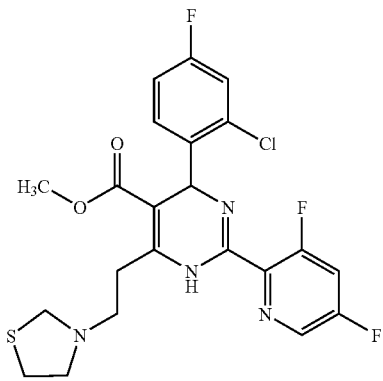

A solution of 0.20 g (0.56 mmol) of the compound from Example IX in 5 ml of isopropanol is heated together with 0.11 g (0.56 mmol) of the compound from Example VI and 0.06 g (0.67 mmol) of sodium acetate under reflux for 2 hours. The reaction mixture is concentrated, and the residue is taken up in ethyl acetate and extracted with dilute hydrochloric acid. The aqueous phase is made alkaline with dilute sodium hydroxide solution and extracted with ethyl acetate. The organic phase is dried over sodium sulfate and concentrated. The residue is chromatographed on silica gel with cyclohexane/ethyl acetate (5:1→3:1) as mobile phase.

Yield: 0.028 g (10.1%)

Melting point: 130° C.

Example 3

Methyl 4-(2-chloro-4-fluorophenyl)-2-(3-fluoro-2-pyridinyl)-6-[2-(4-pyridinyl)-ethyl]-1,4-dihydropyrimidine-5-carboxylate

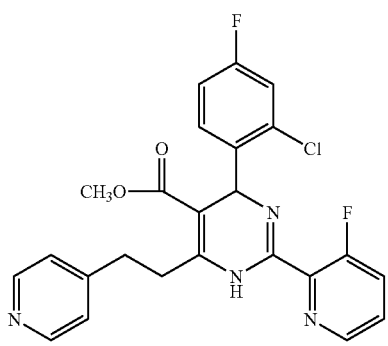

0.60 g (1.73 mmol) of the benzylidene compound from Example XI and 0.30 g (1.73 mmol) of the compound from Example III are heated together with 0.17 g (2.08 mmol) of sodium acetate in 12 ml of isopropanol under reflux overnight. The mixture is concentrated, taken up in dichloromethane and extracted with 2N hydrochloric acid. The aqueous phase is made alkaline with sodium hydroxide solution and extracted with dichloromethane, and the organic phase is washed with aqueous sodium chloride solution, dried over sodium sulfate and concentrated. The residue is chromatographed on silica gel with cyclohexane/ethyl acetate (1:1) as mobile phase, and further purified by crystallization from diethyl ether.

Yield: 0.04 g (5% of theory)

$R_f$=0.79 (dichloromethane/methanol 10:1)

Example 4

Methyl (R)-4-(2-chloro-4-fluorophenyl)-2-(3,5-difluoro-2-pyridyl)-6-piperidinomethyl-1,4-dihydropyrimidine-5-carboxylate

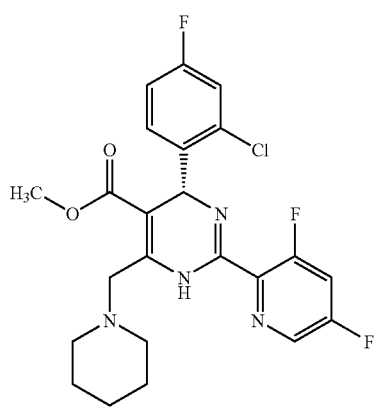

A solution of 100 mg of freshly prepared methyl (R)-6-bromomethyl-4-(2-chloro-4-fluorophenyl)-2-(3,5-difluoro-2-pyridyl)-1,4-dihydropyrimidine-5-carboxylate from Example XIII in 0.5 ml of methanol is mixed with 5 equivalents of piperidine and stirred at room temperature for 30 minutes. The solution is diluted with water and extracted with ethyl acetate.

Yield: 78 mg

Melting point: 132° C.

The compounds listed in the following table were prepared in analogous manner.

| Ex. No. | | m.p. (°C.) | $R_f$ | Mobile phase system |
|---|---|---|---|---|
| 5 | 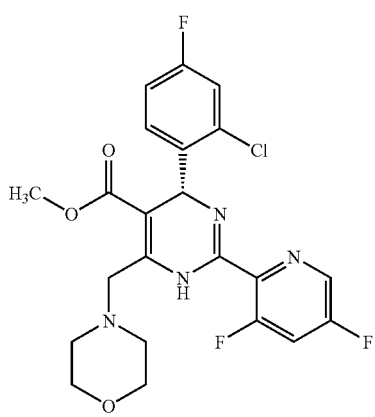 | 178 | | |
| 6 | 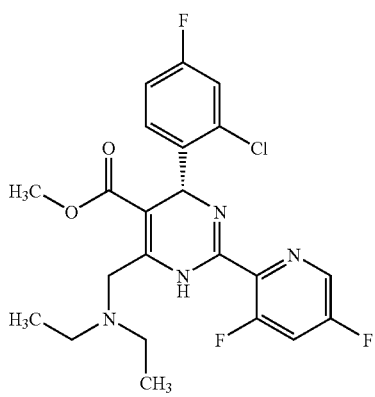 | | 0.46 | B |
| 7 | 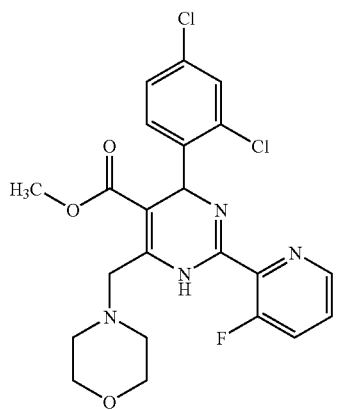 | 182–183 | | |

-continued

| Ex. No. | | m.p. (°C.) | R_f | Mobile phase system |
|---|---|---|---|---|
| 8 | methyl 4-(2,4-dichlorophenyl)-2-(3-fluoropyridin-2-yl)-6-(piperidin-1-ylmethyl)-1,4-dihydropyrimidine-5-carboxylate | 155–156 | | |
| 9 | methyl 4-(2-bromo-4-fluorophenyl)-2-(3,5-difluoropyridin-2-yl)-6-(morpholin-4-ylmethyl)-1,4-dihydropyrimidine-5-carboxylate | 216–218 | | |
| 10 | methyl 4-(2-bromo-4-fluorophenyl)-2-(3,5-difluoropyridin-2-yl)-6-(pyrrolidin-1-ylmethyl)-1,4-dihydropyrimidine-5-carboxylate | 161–162 | | |

-continued

| Ex. No. | | m.p. (°C.) | $R_f$ | Mobile phase system |
|---|---|---|---|---|
| 11 | (structure) | | 0.34 | C |
| 12 | (structure) | 225–227 | | |
| 13 | (structure) | 168–170 | | |

-continued

| Ex. No. | | m.p. (°C.) | R_f | Mobile phase system |
|---|---|---|---|---|
| 14 | [structure] | 189–191 | | |
| 15 | [structure] | 166–168 | | |
| 16 | [structure] | 142–143 | | |

-continued
| Ex. No. | | m.p. (°C.) | $R_f$ | Mobile phase system |
|---|---|---|---|---|
| 17 | 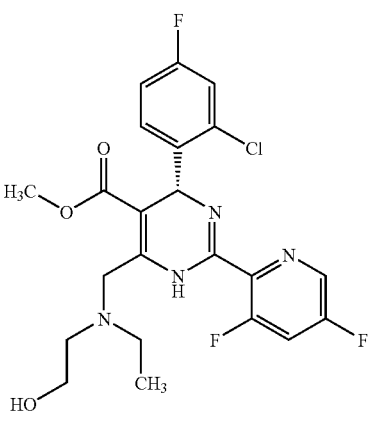 | | 0.13 | E |
| 18 | 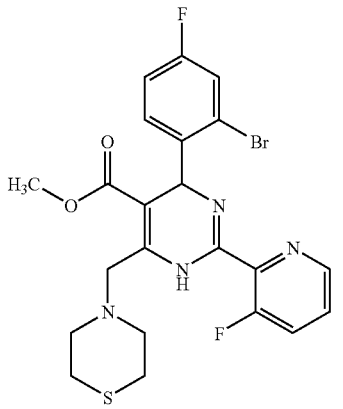 | 128–131 | | |
| 19 | 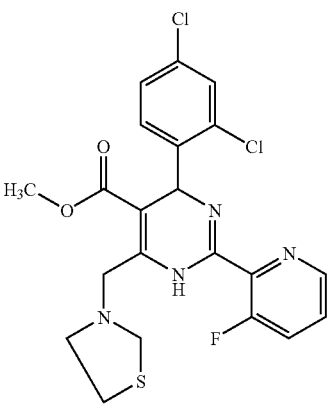 | 175 | | |

-continued

| Ex. No. | | m.p. (°C.) | R$_f$ | Mobile phase system |
|---|---|---|---|---|
| 20 | (structure) | 137 | | |
| 21 | (structure) | 172–173 | | |
| 22 | (structure) | | 0.29 | F |

-continued

| Ex. No. | | m.p. (°C.) | R_f | Mobile phase system |
|---|---|---|---|---|
| 23 | [structure: methyl ester dihydropyrimidine with 4-fluoro-2-chlorophenyl, 3,5-difluoropyridin-2-yl, and CH2-N(CH3)CH2CH2OH substituents] | | 0.20 | F |
| 24 | [structure: methyl ester dihydropyrimidine with 4-fluoro-2-bromophenyl, 3-fluoropyridin-2-yl, and morpholinomethyl substituents] | 156–158 | | |
| 25 | [structure: methyl ester dihydropyrimidine with 4-fluoro-2-chlorophenyl, 3,5-difluoropyridin-2-yl, and azepan-1-ylmethyl substituents] | | 0.60 | G |
| 26 | [structure: methyl ester dihydropyrimidine with 4-fluoro-2-chlorophenyl, 3,5-difluoropyridin-2-yl, and (dimethylamino)methyl substituents] | | 0.07 | C |

-continued

| Ex. No. | | m.p. (°C.) | R_f | Mobile phase system |
|---|---|---|---|---|
| 27 | [structure] | 155 | | |
| 28 | [structure] | 183–184 | | |
| 29 | [structure] | 173–174 | | |

-continued
| Ex. No. | | m.p. (°C.) | $R_f$ | Mobile phase system |
|---|---|---|---|---|
| 30 | 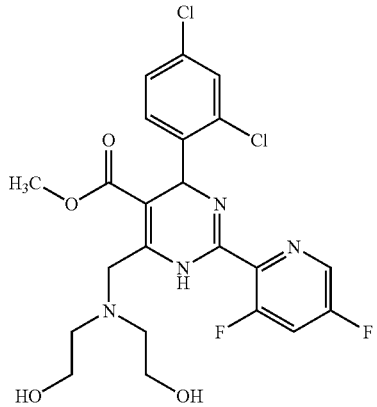 | 144–145 | | |
| 31 | 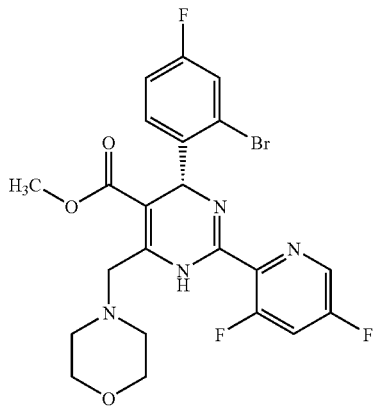 | 189–190 | | |
| 32 | 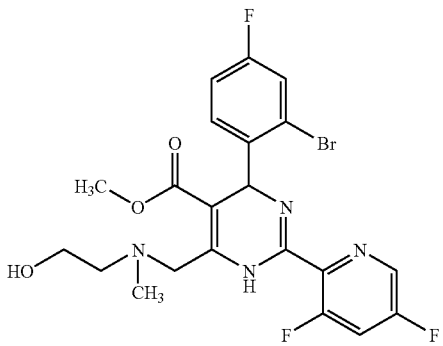 | 114–116 | | |

-continued
| Ex. No. | | m.p. (°C.) | $R_f$ | Mobile phase system |
|---|---|---|---|---|
| 33 | 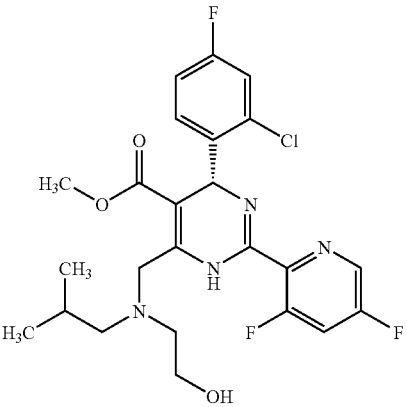 | | 0.54 | E |
| 34 | 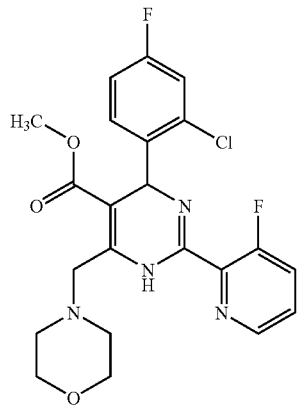 | 161–163 | | |
| 35 | 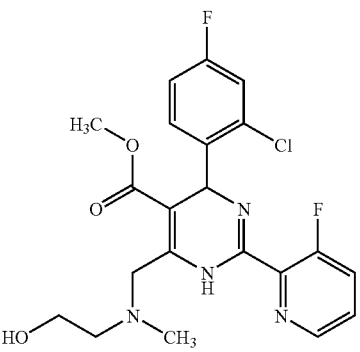 | 117–119 | | |

-continued
| Ex. No. | | m.p. (°C.) | $R_f$ | Mobile phase system |
|---|---|---|---|---|
| 36 | 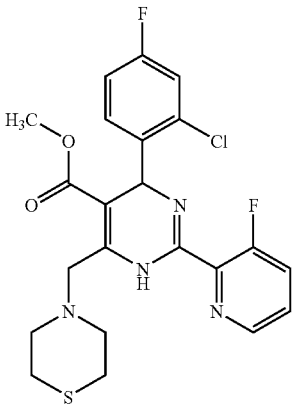 | 145 | | |
| 37 | 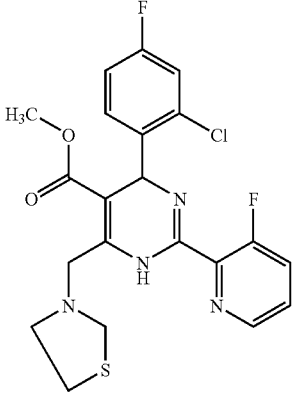 | 163–164 | | |
| 38 | 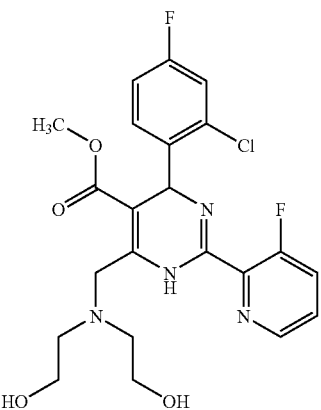 | 119–120 | | |

-continued
| Ex. No. | | m.p. (°C.) | R$_f$ | Mobile phase system |
|---|---|---|---|---|
| 39 | 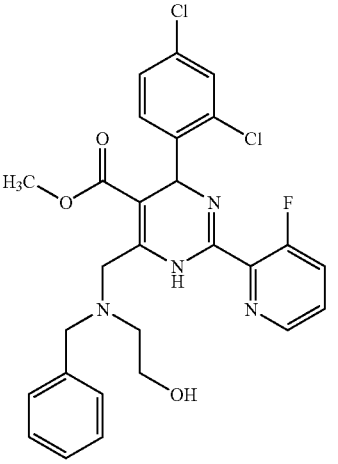 | — | 0.13 | H |
| 40 | 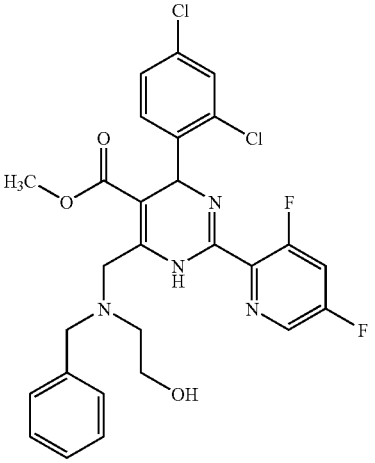 | — | 0.12 | I |
| 41 | 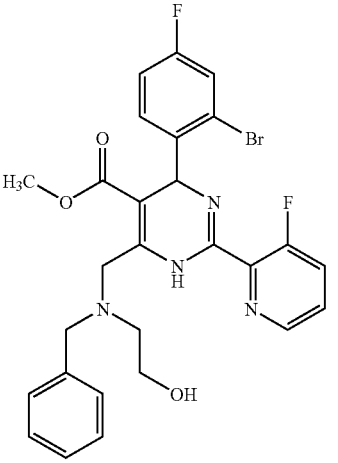 | 121 | | |

-continued

| Ex. No. | | m.p. (°C.) | R_f | Mobile phase system |
|---|---|---|---|---|
| 42 | (structure) | 135 | | |
| 43 | (structure) | 128 | | |
| 44 | (structure) Chiral | | 0.51 | E |

-continued

| Ex. No. | | m.p. (°C.) | R_f | Mobile phase system |
|---|---|---|---|---|
| 45 | [structure] | 149 | | |
| 46 | [structure] | 169–170 | | |
| 47 | [structure] | 133 | | |

-continued

| Ex. No. | | m.p. (°C.) | $R_f$ | Mobile phase system |
|---|---|---|---|---|
| 48 | (structure) | 132 | | |
| 49 | (structure) | | 0.49 | E |
| 50 | (structure) | | 0.21 | F |

-continued
| Ex. No. | | m.p. (°C.) | $R_f$ | Mobile phase system |
|---|---|---|---|---|
| 51 | 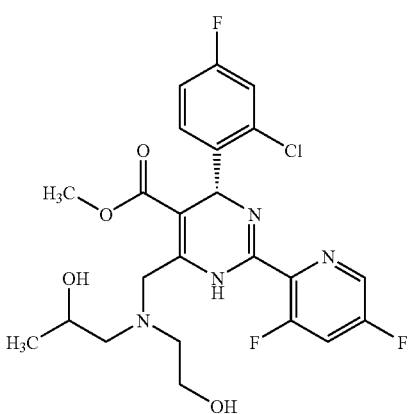 | | 0.23 | F |
| 52 | 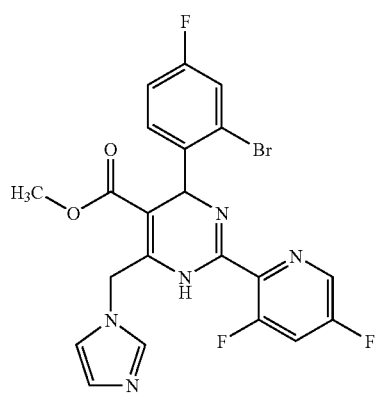 | 123–126 | | |
| 53 | 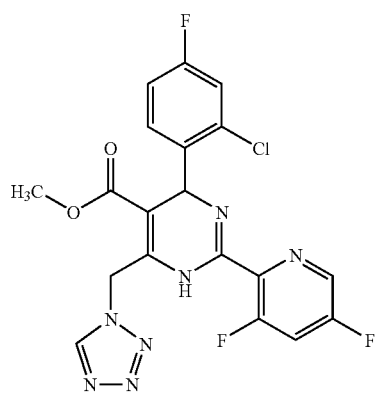 | | 0.18 | C |

-continued

| Ex. No. | | m.p. (°C.) | $R_f$ | Mobile phase system |
|---|---|---|---|---|
| 54 | 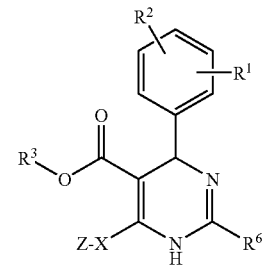 | | 0.44 | C |

| Mobile phase | Abbreviation |
|---|---|
| Cyclohexane/ethyl acetate = 7:3 | A |
| Cyclohexane/ethyl acetate = 8:2 | B |
| Cyclohexane/ethyl acetate = 1:1 | C |
| Cyclohexane/ethyl acetate = 7:3 + drops of $NH_3$ | D |
| Methylene chloride/methanol = 95:5 | E |
| Methylene chloride/methanol = 9:1 | F |
| Toluene/acetone = 1:1 | G |
| Toluene/methanol 10:1 | H |
| Toluene/ethyl acetate = 4:1 | I |
| Methylene chloride/methanol = 10:1 | J |
| Methylene chloride/methanol = 95:5 + drops of $NH_3$ | K |

The activity data for some compounds of the invention are listed below:

| Example No. | $IC_{50}$ (μM) | $Tox_{50}$ (μM) |
|---|---|---|
| 2 | 0.4 | 38 |
| 5 | 0.002 | 40 |
| 7 | 0.025 | 25 |
| 9 | 0.007 | 17 |
| 11 | 0.04 | >8 |
| 15 | 0.05 | 3 |
| 24 | 0.02 | 80 |
| 31 | 0.002 | 63 |
| 34 | 0.009 | 60 |
| 45 | 0.002 | 34 |

The treatment of the hepatitis B virus-producing HepG2.2.15 cells with the compounds of the invention surprisingly led to a reduction in intra- and/or extracellular viral DNA.

The invention claimed is:

1. A compound of the formula

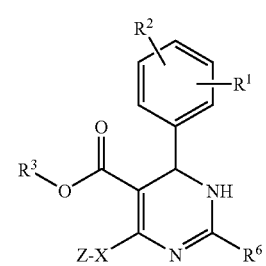

(I)

and the isomeric form thereof (Ia)

in which
R$^1$, R$^2$ are, independently of one another, hydrogen, fluorine, chlorine or bromine,
R$^3$ is $C_1$–$C_4$-alkyl,
X is a methylene or ethylene group,
Z is NR$^4$R$^5$ or pyridyl,
R$^4$ is $C_1$–$C_4$-alkyl which may be substituted by hydroxyl or $C_1$–$C_4$-alkoxycarbonyl, or is benzyl,
R$^5$ is $C_1$–$C_4$-alkyl which may be substituted by hydroxyl, or
R$^4$ and R$^5$ together with the nitrogen atom to which they are bonded are an imidazolyl, triazolyl or tetrazolyl ring or a radical of the formula

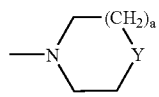

in which
a is zero or 1 and
Y is CH$_2$, CH$_2$CH$_2$, —O— or —S—, and
R$_6$ is pyridyl which is substituted once to twice by fluorine, or is thiazolyl, and the salts thereof.

2. A compound as claimed in claim 1, in which
R$^4$ and R$^5$ together with the nitrogen atom to which they are bonded form a morpholinyl or thiomorpholinyl ring,
and the salts thereof.

3. A compound as claimed in claim 1, in which
R$^1$, R$^2$ are, independently of one another, fluorine, chlorine or bromine,
and the salts thereof.

4. A compound as claimed in claim 1, in which
R$^1$, R$^2$ are, independently of one another, fluorine, chlorine or bromine, and
R$^4$ and R$^5$ together with the nitrogen atom to which they are bonded form a morpholinyl or thiomorpholinyl ring,
and the salts thereof.

5. A compound selected from the group consisting of:

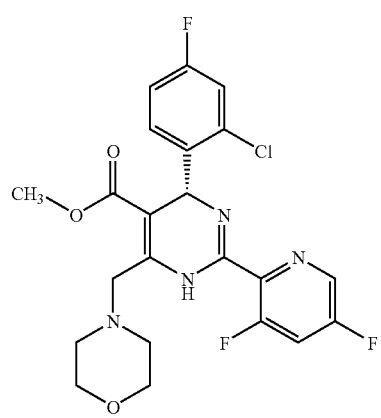

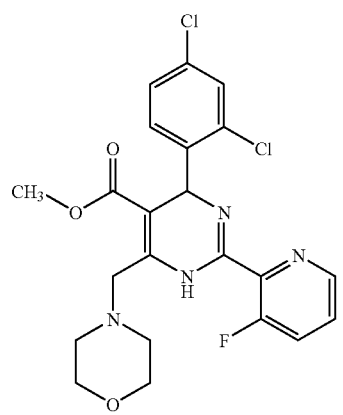

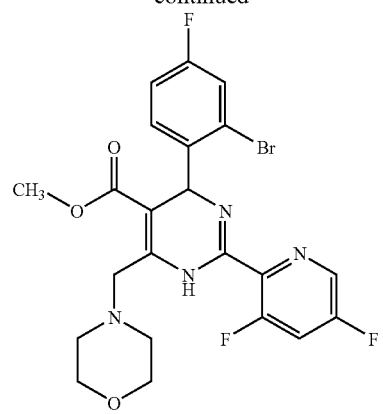

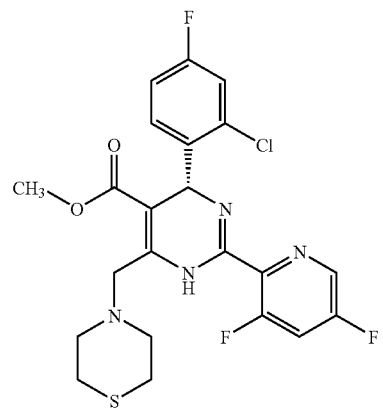

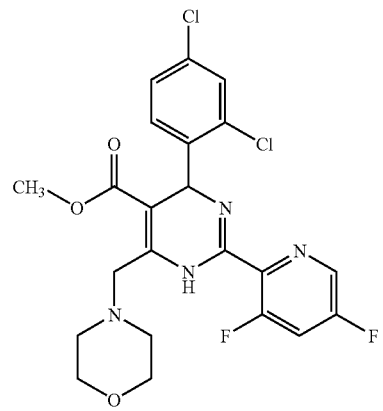

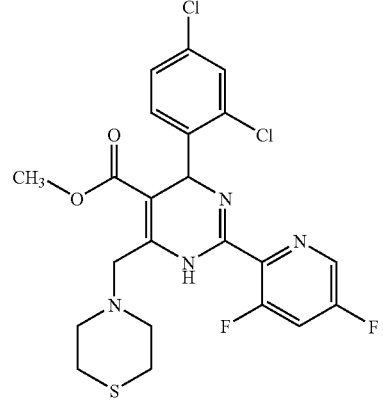

-continued

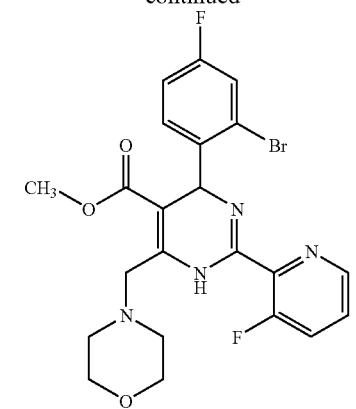

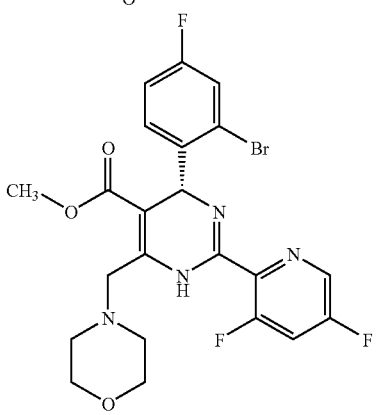

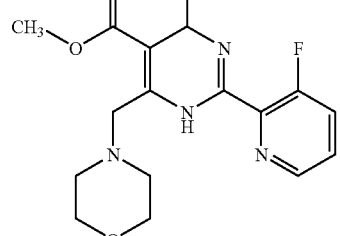

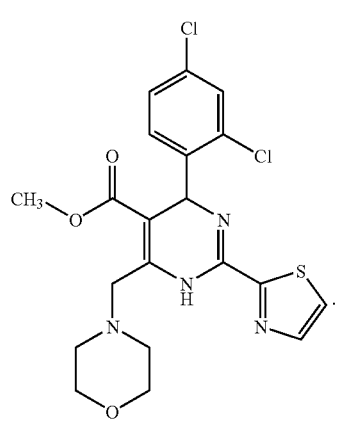

6. A process for preparing the compounds as claimed in claim 1, by

[A] reacting compounds of the formula

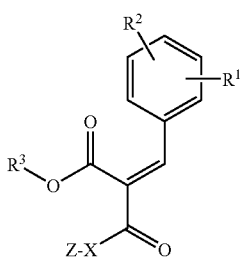 (IV)

in which
R¹ to R³, X and Z have the meanings indicated in claim 1,
with amidines of the formula

 (V)

in which
R⁶ has the meaning indicated in claim 1,
or the salts thereof, or

[B] reacting compounds of the formula

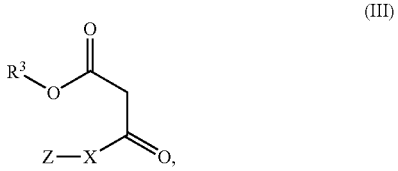 (III)

in which
R³, X and Z have the meanings indicated in claim 1, in a one-stage process with aldehydes of the formula

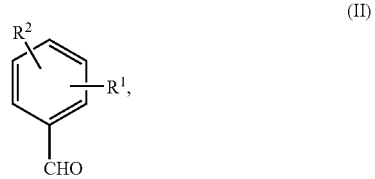 (II)

in which
R¹ and R² have the meanings indicated in claim 1, and amidines of the formula

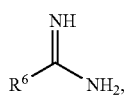

(V)

in which R⁶ has the meanings indicated in claim 1, or the salts thereof, or else

[C] where X in formula (I) is a methylene group, reacting compounds of the formula

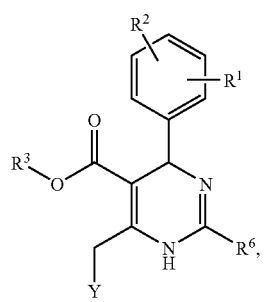

(VI)

in which
R¹ to R³ and R⁶ have the meanings indicated in claim 1, and
Y is a nucleophilically replaceable group,
with compounds of the formula

(VII)

in which
R⁴ and R⁵ have the meanings indicated claim 1, or else

[D] where X in formula (I) is an ethylene group, reacting compounds of the formula

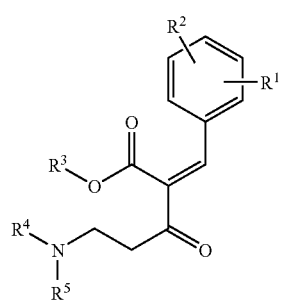

(XII)

in which
R¹ to R⁵ have the meanings indicated in claim 1, with amidines of the formula

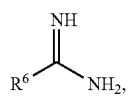

(V)

in which
R⁶ has the meanings indicated in claim 1,
or the salts thereof.

7. A process for preparing the compounds as claimed in claim 1, by

[A] firstly converting aldehydes of the formula

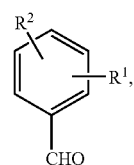

(II)

in which
R¹ and R² have the meanings indicated in claim 1, with β-keto esters of the formula

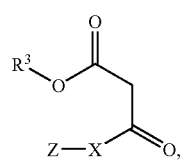

(III)

in which
R³, X and Z have the meanings indicated in claim 1, into benzylidene compounds of the formula

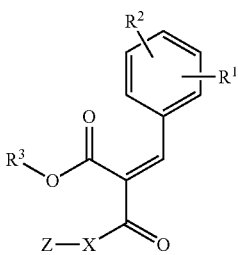

(IV)

and then reacting the latter with amidines of the formula

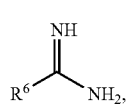

(V)

in which
R⁶ has the meaning indicated in claim 1,
or the salts thereof, or

[B] reacting compounds of the formula (III) in a one-stage process with aldehydes (II) and amidines (V) or the salts thereof, or else

[C] where X in formula (I) is a methylene group, reacting compounds of the formula

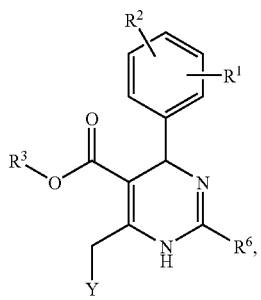 (VI)

in which

R¹ to R³ and R⁶ have the meanings indicated in claim 1, and

Y is a nucleophilically replaceable group, with compounds of the formula

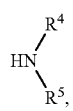 (VII)

in which

R⁴ and R⁴ have the meanings indicated in claim 1, or else

[D] where X in formula (I) is an ethylene group, converting compounds of the formula

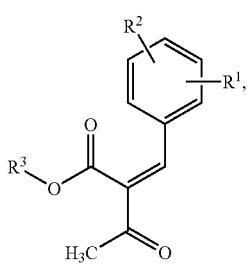 (X)

in which

R¹ to R³ have the meanings indicated in claim 1, with immonium salts of the formula

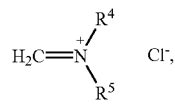 (XI)

in which

R⁴ and R⁵ have the meanings indicated in claim 1, into compounds of the formula

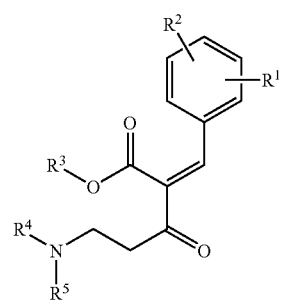 (XII)

and then reacting the latter with amidines of the formula (V) or the salts thereof.

8. A compound of the formula

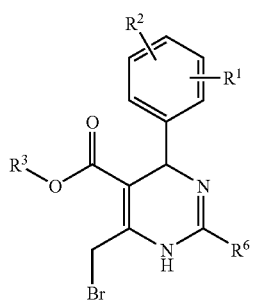 (IX)

in which

R¹, R², R³ and R⁶ have the meanings indicated in claim 1.

9. A method of treating hepatitis B infection, comprising administering to a mammal an effective amount of a compound of claim 1.

10. A method of treating diseases caused by infection with hepatitis B virus, comprising administering to a mammal an effective amount of a compound of claim 1.

11. The method of claim 10 wherein said disease is hepatitis.

12. The method of claim 10 wherein said disease is cirrhosis of the liver.

13. The method of claim 10 wherein said disease is hepatocellular carcinoma.

14. A pharmaceutical preparation comprising one or more compounds of claim 1 in combination with a pharmaceutically acceptable carrier.

* * * * *